United States Patent [19]

Thaler et al.

[11] Patent Number: 5,461,068
[45] Date of Patent: Oct. 24, 1995

[54] IMIDAZOLE DERIVATIVE TINCTURE AND METHOD OF MANUFACTURE

[75] Inventors: Irwin Thaler, Dix Hills; Richard Strauss, Woodbury, both of N.Y.

[73] Assignees: Corwood Laboratories, Inc., Hauppauge; Pedinol Pharmacal, Inc., Farmingdale, both of N.Y.

[21] Appl. No.: 129,462

[22] Filed: Sep. 29, 1993

[51] Int. Cl.$^6$ .................. A61K 31/415; C07D 233/60
[52] U.S. Cl. .................. 514/399; 548/341.1; 548/342.1
[58] Field of Search .................. 514/399, 310; 548/341.1, 342.1; 546/278

[56] References Cited

U.S. PATENT DOCUMENTS

| | | | |
|---|---|---|---|
| 3,717,655 | 2/1973 | Godefroi et al. | 260/309 |
| 4,912,124 | 3/1990 | Das et al. | 514/399 |
| 5,104,893 | 4/1992 | Bononi | 514/399 |
| 5,110,809 | 8/1992 | Wang et al. | 514/399 |

*Primary Examiner*—Herbert J. Lilling
*Attorney, Agent, or Firm*—Darby & Darby

[57] ABSTRACT

A stable solvent system for imidazole derivatives useful in treating antifungal diseases is described. The system comprises a primary carboxylic acid, a polar solvent, a solubilizer, one or more surfactants, and therapeutically effective amounts of an imidazole derivative, preferably miconazole nitrate.

6 Claims, No Drawings

IMIDAZOLE DERIVATIVE TINCTURE AND METHOD OF MANUFACTURE

FIELD OF THE INVENTION

This invention pertains to improved formulations for topical treatment of fungal diseases, and more particularly to solutions of imidazole derivatives of sufficient strength and stability for pharmaceutical use.

BACKGROUND OF THE INVENTION

Fungal infections of the skin, hair and mucosae are mainly caused by dermatophytes, which induce pathologies known collectively as tinea, and by *Candida albicans*, which causes vulvovaginities and oral candidiases ("thrush"), among other syndromes. In recent years, oral candidiases have become more prevalent and intractable due to their appearance in immunocompromised patients, such as those infected with Human immunodeficiency Virus (HIV) or suffering from Acquired Immunodeficiency Syndrome (AIDS).

U.S. Pat. No. 3,717,655 discloses the preparation and use of imidazole derivatives for the topical treatment of fungal infections. 1-[2,4-dichloro-β-(2,4-dichlorobenzyloxy)phenethyl]-imidazole nitrate, whose common name is miconazole nitrate, is disclosed as a broad-spectrum antifungal agent with a powerful activity against dermatophytes and *Candida albicans*.

Miconazole nitrate is currently used in several pharmaceutical forms (ointment, cream, powder, suppositories, etc.). The poor solubility of miconazole and other imidazole derivatives in aqueous solutions such as water and in polar solvents such as ethanol (0.03% and 0.76% weight/volume, respectively), however, forestalls their use in tinctures and sprays and thus limits their applicability to treating a broad range of fungal infections such as those caused by *Trichophyton rubrum, Tricophyton mentagrophytes, Epidermophyton floccsum*, and *Candida albicans*. In order to be pharmaceutically effective, they must be highly soluble ($\geq 2\%$) and remain in solution over a period of time no less than two years.

U.S. Pat. No. 4,912,124 discloses a solvent system for imidazole derivatives employing mixtures of a polar solvent, a polyhydric alcohol that acts as a solubilizing agent, a nonionic or amphoteric surfactant, and a cosmetic humectant. Using this solvent system, solutions containing at least 1% w/v imidazole derivatives can be formulated. A critical aspect of the patent's teaching is the use of a polyhydric alcohol or an ester- or alkyl-substituted derivative therof as a solubilizing agent.

What is needed in the art are improved pharmaceutical formulations comprising imidazole derivatives such as miconazole nitrate in the form of a tincture or spray with improved stability and solubility characteristics, in particular for treatment of fungal infections of the nail bed. Further it is desired that such imidazole derivatives remain in solution for a period of time greater than six months.

SUMMARY OF THE INVENTION

The present invention pertains to a solvent system for imidazole-derived antifungal agents that can accommodate a therapeutically significant concentration of the antifungal agents, and in which the agents will remain stably in solution for extended periods of time. The solvent system comprises 1–2% by weight of a primary carboxylic acid, 20–35% by weight of a polar solvent, 25–35% by weight of a solubilizer, 0–5% by weight of a non-ionic or amphoteric surfactant, and 31–48.5% water, in which imidazole derivatives can be dissolved to 1–4% by weight of the system. Methods for treatment of fungal diseases are also disclosed.

DETAILED DESCRIPTION OF THE INVENTION

The relatively insoluble imidazole derivatives useful for treating fungal infections comprise compounds having the formula:

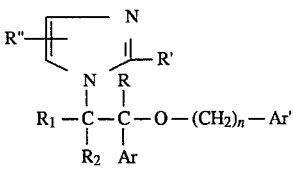

and the therapeutically active acid addition salts thereof, wherein:

R, R1 and R2 are each a member selected from the group consisting of hydrogen and lower alkyl; n is the integer 1 or 2;

Ar is a member selected from the group consisting of phenyl, mon-, di- and tri-halophenyl, lower alkylphenyl, lower alkoxyphenyl, thienyl and halothienyl;

Ar' is a member selected from the group consisting of phenyl, mono-, di- and tri-halophenyl, mon- and di- (lower alkyl) phenyl, lower alkoxyphenyl and cyanophenyl;

R' is a member selected from the group consisting of hydrogen, methyl and ethyl; and R" is a member selected from the group consisting of hydrogen and methyl.

As used herein, "lower alkyl" and "lower alkoxyl" may be straight or branch chained saturated hydrocarbons having from 1 to about 6 carbons, such as, for example, methyl, ethyl, propyl, isopropyl, butyl, pentyl, hexyl and the like alkyls, and, respectively, the corresponding alkoxys such as methoxy, ethoxy, propoxy, isopropoxy, etc. The preferred lower alkyl and lower alkoxy are methyl and methoxy, respectively. The term "halo" refers to halogens of atomic weight less than 127, i.e. fluoro, iodo, bromo, and chloro.

A particularly preferred imidazole ether representative of the above compounds is miconazole, 1-[-2,4-dichloro-β-(2,4-dichlorobenzyloxy)phenethyl] imidazole. The compound is preferably made as the nitrate salt having the formula:

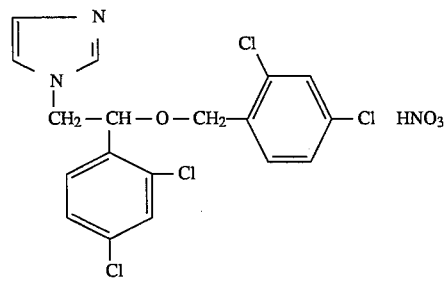

The foregoing imidazole derivatives may be prepared using the processes disclosed in U.S. Pat. No. 3,717,655, which is hereby incorporated by reference.

Heretofore, pharmaceutical formulations incorporating miconazole or miconazole nitrate as the active ingredient have been limited to creams, ointments, powders, and suppositories, due to the low solubility of this agent in aqueous solutions and in alcohols. It has now been found that miconazole can be dissolved in a solvent system comprising a primary carboxylic acid, water, a polar solvent, a solubilizing agent, and a surfactant. The resulting imidazole solution can hold a therapeutically significant concentration of imidazole, and miconazole in particular (at least 2% by weight). The active agent remains stable in such solutions for periods of two years or more.

The solvent system according to this invention comprises
a) a primary carboxylic acid. Primary carboxylic acids that may be used in the invention include, by way of non-limiting examples, acetic acid, glycolic, propionic, or caprylic acid. Acetic acid is the preferred primary carboxylic acid for practicing the present invention.
b) a polar solvent such as benzyl alcohol, ethyl alcohol, isopropyl alchol, butyl alcohol, or mixtures thereof;
c) a solubilizing agent comprising isopropyl alcohol, SDA-40 alcohol (brucine- or brucine sulfate-denatured ethyl alcohol), propylene glycol, or mixtures thereof;
d) a non-ionic or amphoteric surfactant, such as Brij 30 (Laureth-4, the polyethylene glycol ether of lauryl alcohol) or Brij 96 (Oleth-10, the polyethylene glycol ether of oleyl alcohol), and
e) water.

It is noteworthy that the present composition does not employ polyhydric alcohols or their derivatives. The concentration range of each component useful in practicing the present invention is shown in Table 1.

TABLE 1

SOLVENT SYSTEM FOR IMIDAZOLE DERIVATIVES
CONCENTRATION (WEIGHT %)

| | BROAD RANGE | PREFERRED | ESPECIALLY PREFERRED |
|---|---|---|---|
| Carboxylic acid | 1–2 | 1.2–1.8 | 1.5 |
| Polar solvent | 20–35 | 28–32 | 30 |
| Solubilizer | 25–35 | 28–32 | 30 |
| Surfactant | 0–5.0 | 0.5–1.5 | 0.5 |
| Water | Q.S. to 100 | Q.S. to 100 | Q.S. to 100 |

In a preferred embodiment of the present invention, the imidazole derivative is miconazole, having the formula 1-[2,4-dichloro-β-(2,4-dichlorobenzyloxy)phenyethyl]-imidazole. The preferred polar solvent is benzyl alcohol and the primary carboxylic acid is acetic acid. The solubilizing agent is preferably isopropyl alcohol and the surfactant is Brij 30.

The miconazole solution of the present invention is prepared by first mixing the polar solvent and the surfactant, after which glacial acetic acid is added slowly with stirring. The miconazole is then added in small increments, followed by the solubilizing agent. Finally, water is added, and the solution is heated to a temperature ranging between about 40° C. and about 45° C. until the solution becomes clear. Using the solvent system set forth above, solutions of the imidazole derivatives of the present invention having a concentration ranging between about 1% imidazole and about 4% imidazole can be formed. The solutions are stable (i.e. the imidazole remains in solution and biologically active) for periods ranging up to two years or more.

Miconazole and other imidazole derivatives for use in the present invention can be synthesized as described in U.S. Pat. No. 3,717,655, or purchased from American International Chemicals (Natick, Mass.) or R. W. Greeff (Old Greenwich, Conn.).

The antifungal solutions and pharmaceutical formulations of the present invention can be used to treat a wide variety of diseases causes by dermatophytes of the genuses Trichophyton, Microsporum, and Epidermophyton, such as *tinea pedis* or *tinea capitis*, as well as diseases caused by the fungus *Candida albicans*, such as vulvovaginities and "thrush".

Treatment of mammals suffering from the foregoing diseases is effected by topically administering a therapeutically effective amount of the imidazole derivatives of the present invention in the form of tinctures or non-aerosol sprays.

All patents and literature references cited in this specification are hereby incorporated by reference in their entirety. In the case of inconsistencies the present description, including definitions, will prevail.

The present invention is described further in the following specific working examples without limiting the scope thereof. Unless otherwise indicated, all parts and percentages in the examples and specifications are on a weight basis.

EXAMPLE 1

| | weight % |
|---|---|
| Benzyl alcohol, USP | 30.0 |
| Brij 30, USP | 1.0 |
| Glacial acetic acid, USP | 1.5 |
| Miconazole nitrate, USP | 2.0 |
| isopropyl alcohol, USP | 30.0 |
| water | 35.5 |

Benzyl alcohol and Brij 30 were combined and mixed together for 5 minutes, after which the glacial acetic acid was added slowly while the solution was stirred. The miconazole nitrate was then added in increments, allowing each increment to dissolve before subsequent additions, resulting in the formation of a slurry. The isopropyl alcohol was then added to the slurry, and the resulting suspension stirred for about 10–15 minutes. Water was then added (Q.S. to 100% by weight), resulting in a partial clearing of the solution. The mixture was then heated to 40°–45° C. with stirring until the solution became completely clear based on visual assessment. The solution was stored in an airtight container at room temperature.

EXAMPLE 2: STABILITY TESTING

The solution prepared according to Example 1 was subjected to a standard accelerated stability test, using the testing procedure guidelines of the Food and Drug Administration for such materials. That is, the miconazole nitrate solution was maintained at 37°–40° C. in an atmosphere of 65–70% humidity for a period of three months. The miconazole concentration was measured at one-month intervals using high performance liquid chromatography according to the technologies set forth in the U.S.P. or other Compendia for analytical procedures. When tested in this manner, the formulation of Example 1 was found to be stable. The test results indicate that the miconazole nitrate solution of Example 1 has a stability of at least two years under ordinary storage conditions (i.e. room temperature).

EXAMPLE 3: STABILITY OF FORMULATIONS CONTAINING ACETIC ACID

A miconazole nitrate test solution was prepared having the following formulation:

|  | weight % |
|---|---|
| Benzyl alcohol, USP | 30.0 |
| Brij 30, USP | 1.0 |
| Miconazole nitrate, USP | 2.0 |
| isopropyl alcohol, USP | 30.0 |
| water | 37.0 |

The stability of this solution was compared to the stability of the miconazole nitrate solution of Example 1. The test solution does not contain acetic acid but is otherwise identical in formulation. Individual samples of each solution were maintained for one month at 8° C., 25° C., and 40° C., and the solutions were monitored visually for appearance of particulate matter that would indicate a loss of miconazole solubility.

Miconazole was not stable in the test solution lacking acetic acid. In these test solutions, particles were evident at all temperatures within five days. These particles comprise miconazole, with most of the miconazole appearing as a precipitate in the solution maintained at 8° C.

By contrast, the miconazole solution containing acetic acid (as in Example 1) evidenced no particle formation, even after 1 month of incubation at 25° C. and 40° C. A small number of particles were observed after one month of incubation at 8° C.; however, this matter redissolved when the solution was allowed to equilibrate at room temperature.

It is therefore apparent that the presence of a primary carboxylic acid such as acetic acid is important to maintain a stable solution of miconazole suitable for use in fungoid tinctures and sprays. Acetic acid also serves to soften and permeabilize the surface of nails, thus making this formulation particularly effective for treating fungal infections of the nail bed.

What is claimed is:

1. A dermatological antifungal solution comprising:
   a) a solvent system comprising 1–2% by weight of a primary carboxylic acid selected from the group consisting of acetic acid, glycolic acid, propionic acid, and caprylic acid; 20–35% by weight of a polar solvent, selected from the group consisting of benzyl alcohol, ethyl alcohol, isopropyl alcohol, butyl alcohol, and mixtures thereof; 25–35% by weight of a solubilizing agent selected from the group consisting of isopropyl alcohol, SDA-40 alcohol, propylene glycol, and mixtures thereof; 0.5–2.0% by weight of a non-ionic or amphoteric surfactant; and 31–48.5% water;
   b) a therapeutically active amount of an imidazole comprising

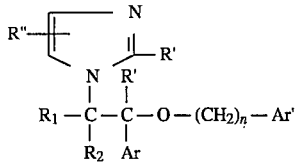

and therapeutically active acid addition salts thereof, wherein:
   R, R1 and R2 are each a member selected from the group consisting of hydrogen and lower alkyl; n is the integer 1 or 2;
   Ar is a member selected from the group consisting of phenyl, mono-, di- and tri-halophenyl, lower alkylphenyl, lower alkoxyphenyl, thienyl and halothienyl;
   Ar' is a member selected from the group consisting of phenyl, mono-, di- and tri-halophenyl, mon- and di-(lower alkyl) phenyl, lower alkoxyphenyl and cyanophenyl;
   R' is a member selected from the group consisting of hydrogen, methyl and ethyl; and
   R" is a member selected from the group consisting of hydrogen and methyl.

2. The dermatological antifungal solution according to claim 1, wherein the therapeutically active agent is stable in solution for at least two years at 25° C.

3. The dermatological antifungal solution according to claim 1, wherein said solvent system comprises 1–2% by weight of the primary carboxylic acid, 28–32% by weight of the polar solvent, 28–32% by weight of the solubilizing agent, and 0.9–1.1% by weight of the surfactant.

4. The dermatological antifungal solution according to claim 1, wherein said surfactant is polyoxyethylene(4) lauryl ether.

5. The dermatological antifungal solution according to claim 1, wherein said therapeutic agent comprises 2% by weight of said solution.

6. The dermatological antifungal solution according to claim 1, wherein said imidazole derivative is miconazole nitrate.

* * * * *